United States Patent
Matsumoto et al.

(10) Patent No.: US 8,984,965 B2
(45) Date of Patent: Mar. 24, 2015

(54) ROTATIONAL TORSION TESTER

(71) Applicants: Sigeru Matsumoto, Tokyo (JP); Hiroshi Miyashita, Tokyo (JP); Kazuhiro Murauchi, Tokyo (JP); Masanobu Hasegawa, Tokyo (JP)

(72) Inventors: Sigeru Matsumoto, Tokyo (JP); Hiroshi Miyashita, Tokyo (JP); Kazuhiro Murauchi, Tokyo (JP); Masanobu Hasegawa, Tokyo (JP)

(73) Assignee: Kokusai Keisokuki Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/049,495

(22) Filed: Oct. 9, 2013

(65) Prior Publication Data
US 2014/0033831 A1      Feb. 6, 2014

Related U.S. Application Data

(63) Continuation-in-part of application No. PCT/JP2012/059777, filed on Apr. 10, 2012.

(30) Foreign Application Priority Data

Apr. 12, 2011  (JP) .................. 2011-088692

(51) Int. Cl.
G01L 3/14      (2006.01)
G01L 3/00      (2006.01)
G01L 1/22      (2006.01)
(Continued)

(52) U.S. Cl.
CPC ........... *G01L 5/0042* (2013.01); *G01M 13/025* (2013.01); *G01N 3/22* (2013.01); *G01L 3/108* (2013.01)
USPC ............. 73/862.338; 73/862.195; 73/862.322

(58) Field of Classification Search
USPC ...................... 73/862.322, 862.195, 862.338
See application file for complete search history.

(56) References Cited

U.S. PATENT DOCUMENTS 4,283,957 A * 8/1981 Zobrist et al. ................... 73/814
4,414,854 A * 11/1983 Haeg ................................ 73/847
(Continued)

FOREIGN PATENT DOCUMENTS

CN  201757732  3/2011
JP  01-262435  10/1989
(Continued)

OTHER PUBLICATIONS

Extended European Search Report issued in Application No. 12771398.0 on Sep. 18, 2014.
(Continued)

*Primary Examiner* — Lisa Caputo
*Assistant Examiner* — Jamel Williams
(74) *Attorney, Agent, or Firm* — McCarter & English, LLP (57) ABSTRACT

A rotational torsion tester, comprising: a first drive shaft; a second drive shaft; a load applying unit that applies a torsional load to a workpiece; at least one bearing unit including a first bearing unit that supports the load applying unit to be rotatable about a rotation axis; a rotation drive unit having a first electric motor that drives the second drive shaft and the load applying unit to rotate in phase; and a torque sensor that detects the torsional load, wherein the load applying unit comprises: a second electric motor that drives the first drive shaft; the torque sensor is attached to a part at which the first drive shaft is inserted into the shaft part; the torque sensor is disposed between a pair of first bearings; and the torque sensor includes a strain gauge adhered to a narrowed part to detect the torsional load.

15 Claims, 9 Drawing Sheets

(51) Int. Cl.
  *G01L 5/00* (2006.01)
  *G01M 13/02* (2006.01)
  *G01N 3/22* (2006.01)
  *G01L 3/10* (2006.01)

(56) References Cited

U.S. PATENT DOCUMENTS

| | | | |
|---|---|---|---|
| 6,378,382 B1 * | 4/2002 | Noguchi et al. | 73/862.29 |
| 6,539,809 B1 * | 4/2003 | Weiss et al. | 73/825 |
| 7,080,565 B2 * | 7/2006 | Delair et al. | 73/862.325 |
| 7,275,419 B2 * | 10/2007 | Raffer | 73/54.28 |
| 7,793,558 B2 * | 9/2010 | Budde | 73/862.627 |
| 2012/0285256 A1 * | 11/2012 | Young et al. | 73/841 |
| 2014/0033831 A1 * | 2/2014 | Matsumoto et al. | 73/862.338 |
| 2014/0208863 A1 * | 7/2014 | Matsumoto et al. | 73/847 |
| 2014/0208864 A1 * | 7/2014 | Matsumoto et al. | 73/848 |
| 2014/0257781 A1 * | 9/2014 | Matsumoto et al. | 703/7 |

FOREIGN PATENT DOCUMENTS

| | | |
|---|---|---|
| JP | 03-200043 | 9/1991 |
| JP | 5-090345 | 12/1993 |
| JP | 10-274610 | 10/1998 |
| JP | 2000-074806 | 3/2000 |
| JP | 2001-138146 | 5/2001 |
| JP | 2002-214080 | 7/2002 |
| JP | 2004-125549 | 4/2004 |
| JP | 2006-214795 | 8/2006 |
| JP | 2008-267939 | 11/2008 |
| WO | 2010/049175 | 5/2010 |

OTHER PUBLICATIONS

International Search Report issued in PCT/JP2012/059777 on Jul. 3, 2012.
Chinese Office Action issued in Chinese Application No. 201280025283.4 dated Nov. 15, 2014.

* cited by examiner

ROTATIONAL TORSION TESTER

This is a Continuation-in-Part of International Application No. PCT/JP2012/059777 filed Apr. 10, 2012, which claims priority from Japanese Patent Application No. 2011-088692 filed Apr. 12, 2011. The entire disclosure of the prior application is hereby incorporated by reference herein its entirety.

TECHNICAL FIELD

The present invention relates to a rotational torsion tester configured to give torsion in a rotational direction to a test piece while rotating the test piece.

BACKGROUND

A power transmission component, such as a clutch or a propeller shaft, receives varying torque about a rotation axis in a state where the power transmission component rotates at a high speed. In order to accurately evaluate the fatigue resistance of such a component, a rotational torsion test where torque (a torsion load) is applied to a test piece about the rotation axis while rotating the test piece is performed.

Japanese Patent Provisional Publication No. 2004-125549A (hereafter, referred to as patent document 1) discloses a rotational torsion tester including a hydraulic actuator 52 which applies torque to a test piece 11, and an AC motor 58 which rotates the hydraulic actuator 52 and the test piece 11 in a synchronized manner. The AC motor 58 rotates a main body of the hydraulic actuator 52, and rotates an output shaft of the test piece 11 coaxially at the same speed as that of the main body of the hydraulic actuator 52. An output shaft of the hydraulic actuator 52 is coupled to an input shaft of the test piece 11, so that, by driving the AC motor 58 and the hydraulic actuator 52, torque can be applied to the test piece 11 while rotating the test piece 11. The torque applied to the test piece 11 is measured by a torque detector 47 provided between the output shaft 46 and the test piece 11.

SUMMARY

The tester described in patent document 1 is configured such that the test piece 11 and an attachment flange for attaching the test piece 11 are supported by the tester via the torque detector 47. Therefore, to the torque detector 47, a torsion load to be measured as well as a bending load caused by gravity and a centrifugal force of the test piece 11 and the attachment flange are applied. As a result, it becomes difficult to adequately accurately measure the torque applied to the test piece 11 during the testing.

The present invention is advantageous in that it provides a rotational torsion tester configured to accurately measure torque applied to a test piece during testing.

According an aspect of the invention, there is provided a rotational torsion tester, comprising: a first drive shaft that rotates about a predetermined rotation axis, an end of a workpiece being attached to the first drive shaft; a second drive shaft that rotates about the predetermined rotation axis, the other end of the workpiece being attached to the second drive shaft; a load applying unit that applies a torsional load to the workpiece by driving and rotating the first drive shaft; at least one bearing unit including a first bearing unit that supports the load applying unit to be rotatable about the predetermined rotation axis; a rotation drive unit having a first electric motor that drives the second drive shaft and the load applying unit to rotate in phase; and a torque sensor that detects the torsional load. In this configuration, by causing the rotation drive unit to rotate the workpiece via the first drive shaft and the second drive shaft and by causing the load applying unit to give a phase difference to rotations of the first drive shaft and the second drive shaft, a load is applied to the workpiece. The load applying unit comprises: a second electric motor that drives the first drive shaft; and a frame having a cylindrical shaft part into which the first drive shaft is inserted; the frame is supported by the first bearing unit at the shaft part and the frame supports the first drive shaft; the torque sensor is attached to a part at which the first drive shaft is inserted into the shaft part, and detects the torsion load at the part; the shaft part includes a pair of first bearings which are disposed to be away from each other in an axial direction and rotatably support the first drive shaft; a narrowed part formed to have a decreased diameter is formed at the part at which the first drive shaft is situated in the shaft part; and the torque sensor includes a strain gauge adhered to the narrowed part to detect the torsion load.

According to the above described configuration, the portion at which the torsion load is detected has a high degree of rigidity. Therefore, a detection error of the torque sensor due to gravity and a centrifugal force of the test piece can be suppressed, and thereby the torque load can be measured with a high degree of accuracy.

The first bearing unit may comprise a pair of second bearings which are disposed to be away from each other in the axial direction and rotatably support the shaft part; and the torque sensor is disposed between the part of second bearings.

The load applying unit may comprise a drive amount detection unit configured to detect a drive amount of the second electric motor.

The rotational torsion tester may further comprise: a drive power supply unit that is disposed outside the load applying unit and is configured to supply driving power to the second electric motor; a drive power transmission line configured to transmit the driving power from the drive power supply unit to the second electric motor; a torque signal processing unit that is disposed outside the load applying unit and is configured to process a torque signal outputted by the torque sensor; and a torque signal transmission line configured to transmit the torque signal from the torque sensor to the torque signal processing unit. The drive power transmission line may comprise: an outer drive power transmission line disposed outside the load applying unit; an internal drive power transmission line that is disposed in an inside of the load applying unit and is configured to rotate together with the load applying unit; and a first slip ring part that connects the outer drive power transmission line with the internal drive power transmission line. The torque signal transmission line may comprise: an outer torque signal transmission line disposed outside the load applying unit; an internal torque signal transmission line that is disposed in an inside of the load applying unit and is configured to rotate together with the load applying unit; and a second slip ring part that connects the outer torque signal transmission line with the internal torque signal transmission line. The second slip ring part may be disposed to be away from the first slip ring part.

The at least one bearing unit may be disposed between the first slip ring part and the second slip ring part.

The shaft part may have a groove extending in the axial direction from the narrowed part; and the internal torque signal transmission line may be formed to pass through the groove from the narrowed part, and may be connected to a ring-shaped electrode of the second slip ring part.

The rotational torsion tester may further comprise a drive amount signal transmission line configured to transmit a signal outputted by the drive amount detection unit to the drive power supply unit. In this case, the drive amount signal transmission line may comprise: an outer drive amount signal transmission line disposed outside the load applying unit; an internal drive amount signal transmission line that is wired in an inside of the load applying unit and is configured to rotate together with the load applying unit; and a third slip ring part that is disposed to be away from the first slip ring part and is configured to connect the outer drive amount signal transmission line with the internal drive amount signal transmission line.

The rotational torsion tester may further comprise a rotation number detection unit configured to detect a number of rotations of the load applying unit. In this case, the at least one bearing unit may be disposed between the rotation number detection unit and the first slip ring part.

The rotation drive unit may comprise a drive force transmission unit configured to transmit a driving force of the first electric motor to the load applying unit and the second drive shaft. In this case, the drive force transmission unit may comprise: a first drive force transmission unit configured to transmit the driving force of the first electric motor to the second drive shaft; and a second drive force transmission unit configured to transmit the driving force of the first electric motor to the load applying unit.

Each of the first drive force transmission unit and the second drive force transmission unit may comprise at least one of an endless belt mechanism, a chain mechanism and a gear mechanism.

Each of the first drive force transmission unit and the second drive force transmission unit may comprise the endless belt mechanism. The first drive force transmission unit may comprise: a third drive shaft that is disposed to be parallel with the predetermined rotation axis and is configured to be driven by the first electric motor; a first drive pulley fixed to be coaxial with the third drive shaft; a first driven pulley fixed to be coaxial with the load applying unit; and a first endless belt provided to extend between the first drive pulley and the first driven pulley. The second drive force transmission unit may comprise: a fourth drive shaft that is coaxially coupled to the third drive shaft; a second drive pulley fixed to the fourth drive shaft; a second driven pulley fixed to the first drive shaft; and a second endless belt provided to extend between the second drive pulley and the second driven pulley.

The first driven pulley may be formed on an outer circumferential surface of the frame of the load applying unit.

The rotational torsion tester may further comprise a reduction gear disposed in the load applying unit. In this case, the first driven pulley may be fixed to a reduction gear fixing plate to which the reduction gear is attached.

The first drive shaft and the frame of the load applying unit may be connected to each other coaxially and integrally.

The frame of the load applying unit may have a cylindrical part whose outer circumferential surface is formed in a cylindrical shape to be coaxially with the predetermined rotation axis. In this case, the rotational torsion tester may further comprise: a third drive shaft that is disposed to be parallel with the predetermined rotation axis and is configured to be driven by the first electric motor; a first drive pulley fixed to the third drive shaft; and a timing belt wound around the first drive pulley and the cylindrical part of the frame.

DETAILED DESCRIPTION OF EMBODIMENTS

Hereafter, a rotational torsion tester according to embodiments of the invention is described with reference to the accompanying drawings.

First Embodiment

Figure 1:
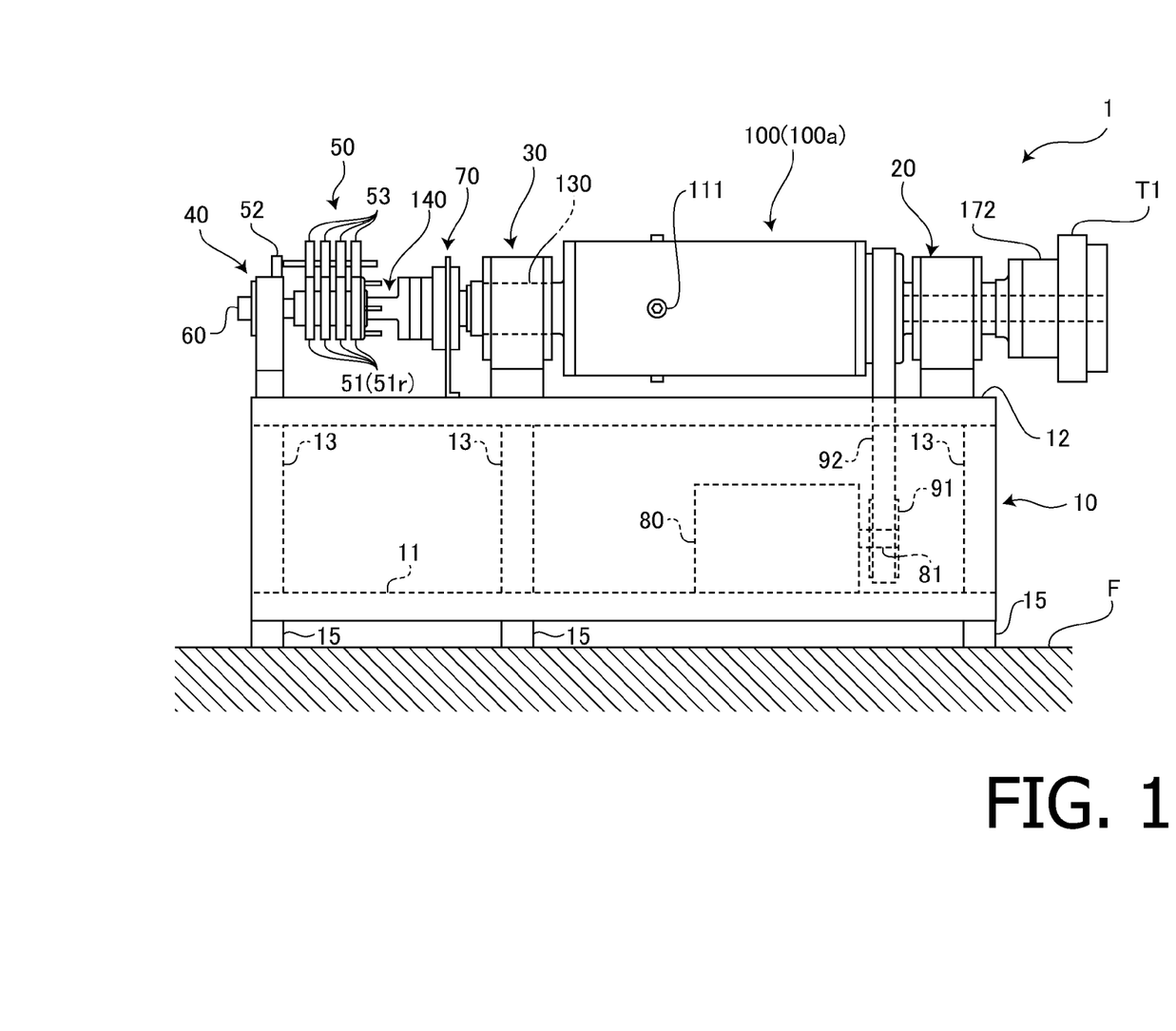
FIG. 1 is a side view of a rotational torsion tester according to a first embodiment of the invention.

FIG. 1 is a side view of a rotational torsion tester 1 according to a first embodiment of the invention. The rotational torsion tester 1 is an apparatus for performing a rotational torsion test for a test piece 1 being a vehicle clutch, and is able to apply set fixed or varying torque to a portion between an input shaft and an output shaft of the test piece T1 (e.g., between a clutch cover and a clutch disk) while rotating the test piece T1. The rotational torsion tester 1 includes a stage 10 which supports each part of the rotational torsion tester 1, a load applying unit 100 which applies predetermined torque to the test piece T1 while rotating together with the test piece T1, bearing units 20, 30 and 40 which support the load applying unit 100 to be rotatable, slip ring parts 50 and 60 which electrically connect parts outside the load applying unit 100 with parts inside the load applying unit 100, a rotary encoder 70 which detects the number of rotations of the load applying unit 100, an inverter motor 80 which drives and rotates the load applying unit 100 at a set speed in a set direction, a drive pulley 91 and a drive belt (timing belt) 92.

The stage 10 includes a lower base plate 11 and an upper base plate 12 arranged in the up and down direction to be parallel with each other, and a plurality of vertical support walls 13 which couples the lower base plate 11 with the upper base plate 12. A plurality of vibration absorption mounts 15 is disposed on a lower surface of the lower base plate 11, and the stage 10 is disposed on a flat floor F via the vibration absorption mounts 15. On an upper surface of the lower base plate 11, the inverter motor 80 is fixed. To an upper surface of the upper base plate 12, the bearing units 20, 30 and 40 and the rotary encoder 70 are attached.

Figure 2:
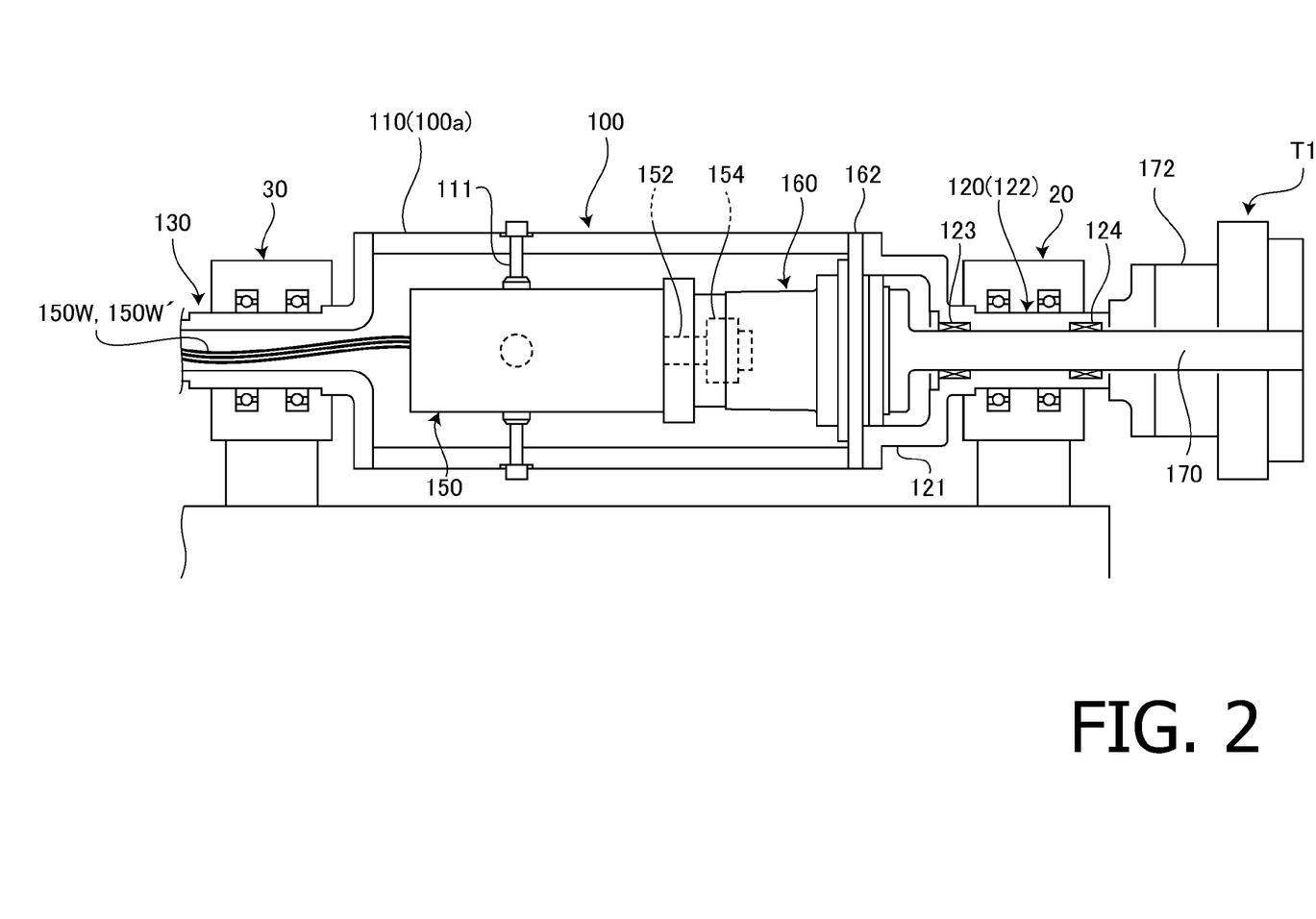
FIG. 2 is a vertical cross section around a load applying unit in the rotational torsion tester.

FIG. 2 is a vertical cross section around the load applying unit 100 of the rotational torsion tester 1. The load applying unit 100 includes a stepped cylindrical casing 100a, a servo motor 150 attached to the casing 100a, a reduction gear 160 and a joint shaft 170, and a torque sensor 172. The casing 100a includes a motor accommodation unit (a body section) 110, a shaft part 120 rotatably supported by the bearing unit 20, a shaft part 130 rotatably supported by the bearing unit 30, and a shaft part 140 to which a slip ring 51 of the slip ring part 50 (FIG. 1) is attached. Each of the motor accommodation unit 110 and the shaft parts 120, 130 and 130 is a cylindrical member (or a stepped cylindrical part whose diameter changes in a staircase pattern) having a hollow part. The motor accommodation unit 110 is a component having the largest diameter and accommodates the servo motor 150 in the hollow part. The shaft part 120 is connected to one end of the motor accommodation unit 110 on a test piece T1 side, and the shaft part 130 is connected to the other end of the motor accommodation unit 110. To an opposite side end of the shaft part 130 with respect to the motor accommodation unit 110, the shaft part 140 is connected. The shaft part 140 is rotatably supported by the bearing unit 40 at a tip end thereof (a left end in FIG. 1).

The servo motor 150 is fixed to the motor accommodation unit 110 with a plurality of fixing bolts 111. A drive shaft 152 of the servo motor 150 is coupled to an input shaft of the reduction gear 160 via a coupling 154. The joint shaft 170 is connected to an output shaft of the reduction gear 160. The reduction gear 160 is provided with an attachment flange 162, and is fixed to the casing 100*a* by fastening the motor accommodation unit 110 and the shaft part 120 with bolts (not shown) in a state where the attachment flange 162 is sandwiched between the motor accommodation unit 110 and the shaft part 120.

The shaft part 120 which is a stepped cylindrical member has a pulley part 121 having a large diameter on the motor accommodation unit 110 side, and a main shaft part 122 rotatably supported by the bearing unit 20 on the test piece T1 side. As shown in FIG. 1, the drive belt 92 is provided to extend between the outer circumferential surface of the pulley part 121 and the drive pulley 91 attached to a drive shaft 81 of the inverter motor 80. A driving force of the inverter motor 80 is transmitted to the pulley part 121 through the drive belt 92 to rotate the load applying unit 100. In the pulley part 121, a joint part of the reduction gear 160 and the joint shaft 170 is accommodated. By utilizing, as a pulley, a portion at which the outer diameter needs to be increased to accommodate the joint part, a compact apparatus configuration can be realized without increasing the number of parts.

To a tip (a right end in FIG. 2) of the main shaft part 122 of the shat part 120, the torque sensor 172 is attached. A surface (a right side surface in FIG. 2) of the torque sensor 172 is formed as a seating face to which the input shaft (clutch cover) of the test piece T1 is attached, and the torque applied to the test piece T1 is detected by the torque sensor 172.

On an inner circumferential surface of the main shaft part 122 of the shaft part 120, bearings 123 and 124 are provided respectively near the both ends in the axial direction. The tip (a right end in FIG. 2) of the joint shaft 170 protrudes outward while penetrating through the torque sensor 172. The protruded part from the torque sensor 172 is fixed by being inserted into a shaft hole of a clutch disc (a clutch hub) being the output shaft of the test piece T1. That is, by rotating the joint shaft 170 with respect to the casing 100*a* of the load applying unit 100 through the servo motor 150, set dynamic or static torque can be applied between the input shaft (clutch cover) of the test piece T1 fixed to the casing 100*a* and the output shaft (clutch disc) of the test piece T1 fixed to the joint shaft 170.

As shown in FIG. 1, near the end (a left end in FIG. 1) of the shaft part 130, the rotary encoder 70 for detecting the number of rotations of the load applying unit 100 is disposed.

To a central portion of the shaft part 140, the slip ring 51 of the slip ring part 50 is attached. To the slip ring 51, a power line 150W (FIG. 2) which supplies a driving current to the servo motor 150 is connected. The power line extending from the servo motor 150 is connected to the slip ring 51 via the hollow parts formed in the shaft parts 130 and 140.

The slip ring part 50 includes the slip ring 51, a brush fixing member 52 and four brushes 53. As described above, the slip ring 51 is attached to the shaft part 140 of the load applying unit 100. The brushes 53 are fixed to the bearing unit 40 by the brush fixing member 52. The slip ring 51 has four electrode rings 51*y* arranged to have constant intervals therebetween in the axial direction, and the brushes 53 are arranged to face the respective electrode rings 51*r*. The power line 150W of the servo motor 150 is conned to each electrode ring 51*r*, and each terminal of the brush is connected to a servo motor drive unit 330 (which is described later). That is, the power line 150W of the servo motor 150 is connected to the servo motor drive unit 330 via the slip ring part 50. The slip ring part 50 guides the drive current of the servo motor 150 supplied by the servo motor drive unit 330, to the inside of the rotating load applying unit 100.

To the tip (the left end in FIG. 1) of the shaft part 140, a slip ring (not shown) of the slip ring part 60 is attached. To the slip ring of the slip ring part 60, a communication line 150W' (FIG. 2) extending from the servo motor 150 is connected. For example, a signal of a built-in rotary encoder (not shown) provided in the servo motor 150 is outputted to the outside via the slip ring part 60. If a large current, such as a driving current for a large-size motor, flows through a slip ring, large electromagnetic noise tends to occur. Furthermore, the slip ring is susceptible to electromagnetic noise because the slip ring is not shielded adequately. Thanks to the above described configuration where the communication line 150' through which a weak current flows and the power line 150W through which a large current flows are connected to the external wirings by using separate slip rings arranged to have a certain distance therebetween, nose can be effectively prevented from mixing into a communication signal. In this embodiment, the slip ring part 60 is provided on an opposite surface with respect to the slip ring part 50 side of the bearing unit 40. As a result, the bearing unit 40 also provides advantageous effect that the slip ring part 60 is shielded from the electromagnetic noise being produced in the slip ring part 50.

Figure 3:
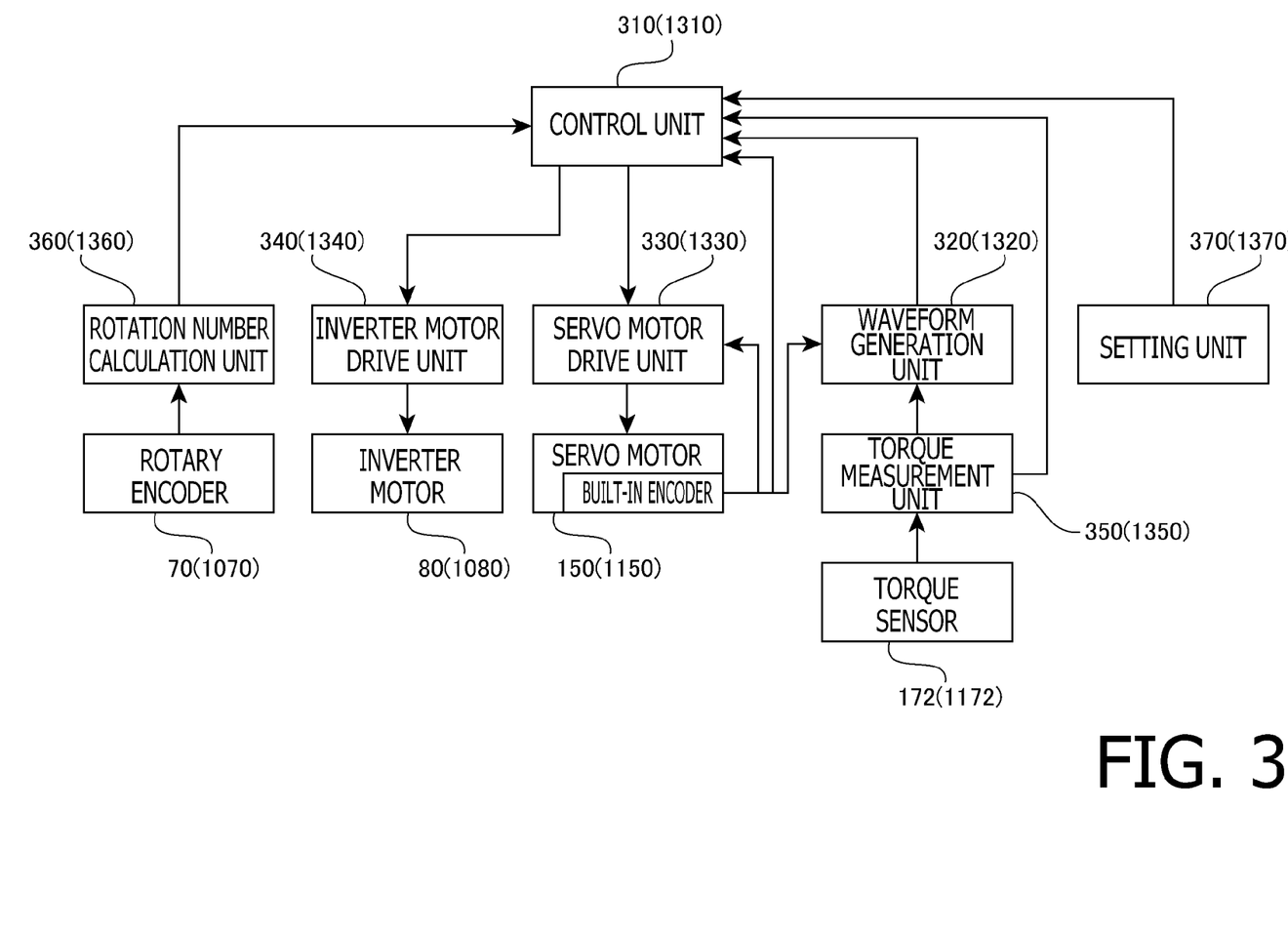
FIG. 3 is a block diagram generally illustrating a configuration of a control system of the rotational torsion tester.

Next, a control system of the rotational torsion tester 1 is explained. FIG. 3 is a block diagram generally illustrating a configuration of the control system of the rotational torsion tester 1. The rotational torsion tester 1 includes a control unit 310 which entirely controls the rotational torsion tester 1, a setting unit 370 for setting various test conditions, a waveform generation unit 320 which calculates a waveform for the drive amount of the servo motor 150 based on the set test condition and outputs the waveform to the control unit 310, the servo motor drive unit 330 which generates the drive current for the servo motor 150 based on control from the control unit 310, an inverter motor drive unit 340 which generates the drive current for the inverter motor 80 based on the control by the control unit 310, a torque measurement unit 350 which calculates the torque being applied to the test piece T1 based on the signal from the torque sensor 350, and a rotation number calculation unit 360 which calculates the number of rotations of the load applying unit 100 based on the signal from the rotary encoder 70.

The setting unit 370 includes a user input interface, such as a touch panel (not shown), a removable record media reading device, such as a CD-ROM drive, an external input interface, such as a GPIB (General Purpose Interface Bus) or a USB (Universal Serial Bus), and a network interface. The setting unit 370 makes settings for the test condition based on a user input received through the user input interface, data read from the removal record media, data inputted from an external device (i.e., a function generator) via the external input interface, and/or data obtained from a server via the network interface. The rotational torsion tester 1 according to the embodiment supports two types of control including displacement control where the torsion given to the test piece T1 is controlled based on a torsion angle applied to the test piece T1 (i.e., a drive amount of the servo motor 150 detected by the built-in rotary encoder provided in the servo motor 150), and torque control where the torsion given to the test piece T1 is controlled based on the torque being applied to the test piece T1 (i.e., the torque detected buy the torque sensor 172). It is possible to make settings, through the setting unit 370, as to which of the control manners should be used.

Based on the setting value for the number of rotations of the test piece T1 obtained from the setting unit 370, the control unit 310 instructs the inverter motor drive unit 340 to execute rotation driving for the inverter motor 80. Furthermore, based on the waveform data of the drive amount of the servo motor 150 obtained from the waveform generation unit 320, the control unit 310 instructs the servo motor drive unit 330 to execute driving of the servo motor 150.

As shown in FIG. 3, a measured value of the torque calculated by the torque measurement unit 350 based on the signal of the torque sensor 172 is transmitted to the control unit 310 and the waveform generation unit 320. The signal of the built-in rotary encoder provided in the servo motor 150 is transmitted to the control unit 310, the waveform generation unit 320 and the servo motor drive unit 330. The waveform generation unit 320 calculates the measured value of the number revolutions of the servo motor 150 from the signal of the built-in rotary encoder which detects the rotation angle of the drive shaft 152 of the servo motor 150. For the torque control, the waveform generation unit 320 compares the setting value of the torque with the measured value of the torque (for the displacement control, the drive amount of the servo motor), and executes feedback control for the setting value of the drive amount of the servo motor 150 transmitted to the control unit 310 so that the setting value and the measured value of the torque become equal to each other.

The measured value of the number of rotations of the load applying unit 100 calculated by the rotation number calculation unit 360 based on the signal of the rotary encoder 70 is transmitted to the control unit 310. The control unit 310 compares the setting value and the measured value of the number of rotations of the load applying unit 100, and executes feedback control for the frequency of the drive current transmitted to the inverter motor 80 so that the setting value and the measured value of the number of rotations become equal to each other.

The servo motor drive unit 330 compares a target value of the drive amount of the servo motor 150 with the drive amount detected by the built-in rotary encoder, and executes feedback control for the drive current transmitted to the servo motor 150 so that the drive amount approaches the target value.

The control unit 310 includes a hard disk drive (not shown) for storing test data, and records the measured values of the rotation speed of the test piece T1 and the torsion angle (the rotation angle of the servo motor 150) and the torsion load applied to the test piece T1 in the hard disk drive. Change of each measured value over time is recorded throughout the time period from the start to end of the test. By the above described configuration of the first embodiment described above, the rotational torsion test is performed for the clutch of a vehicle being the test piece T1.

Second Embodiment

Figure 4:
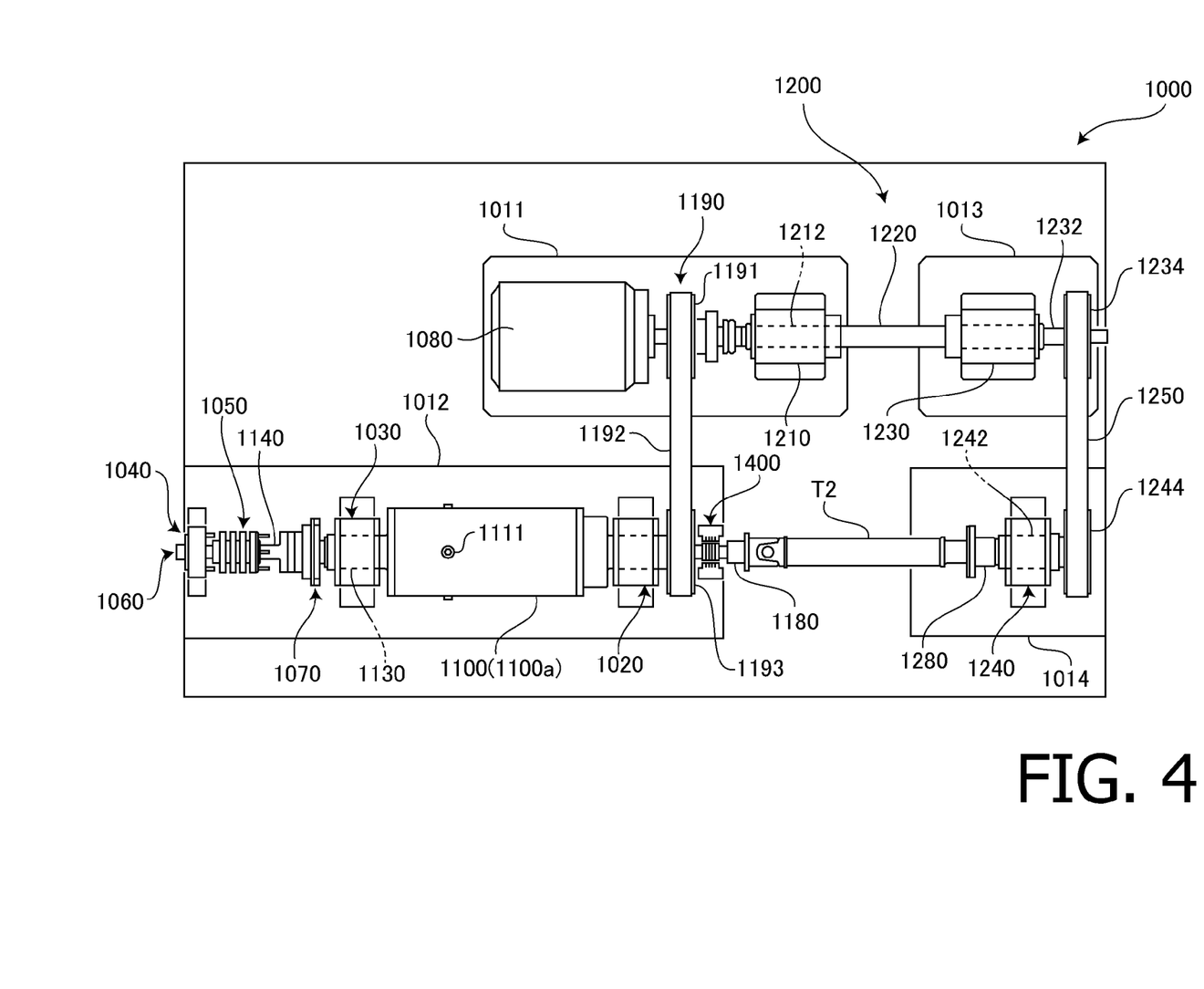
FIG. 4 is a plan view of a rotational torsion tester according to a second embodiment of the invention.
Figure 5:
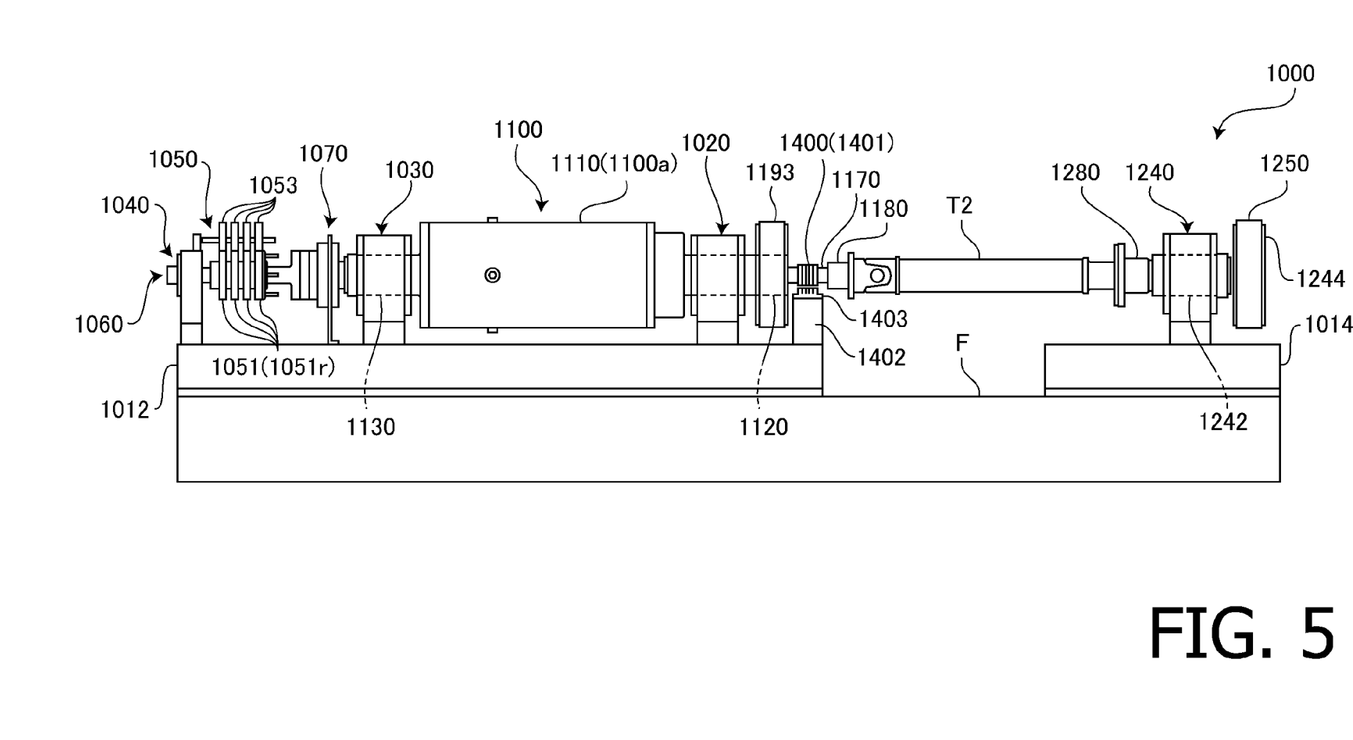
FIG. 5 is a side view of the rotational torsion tester according to the second embodiment.
Figure 6:
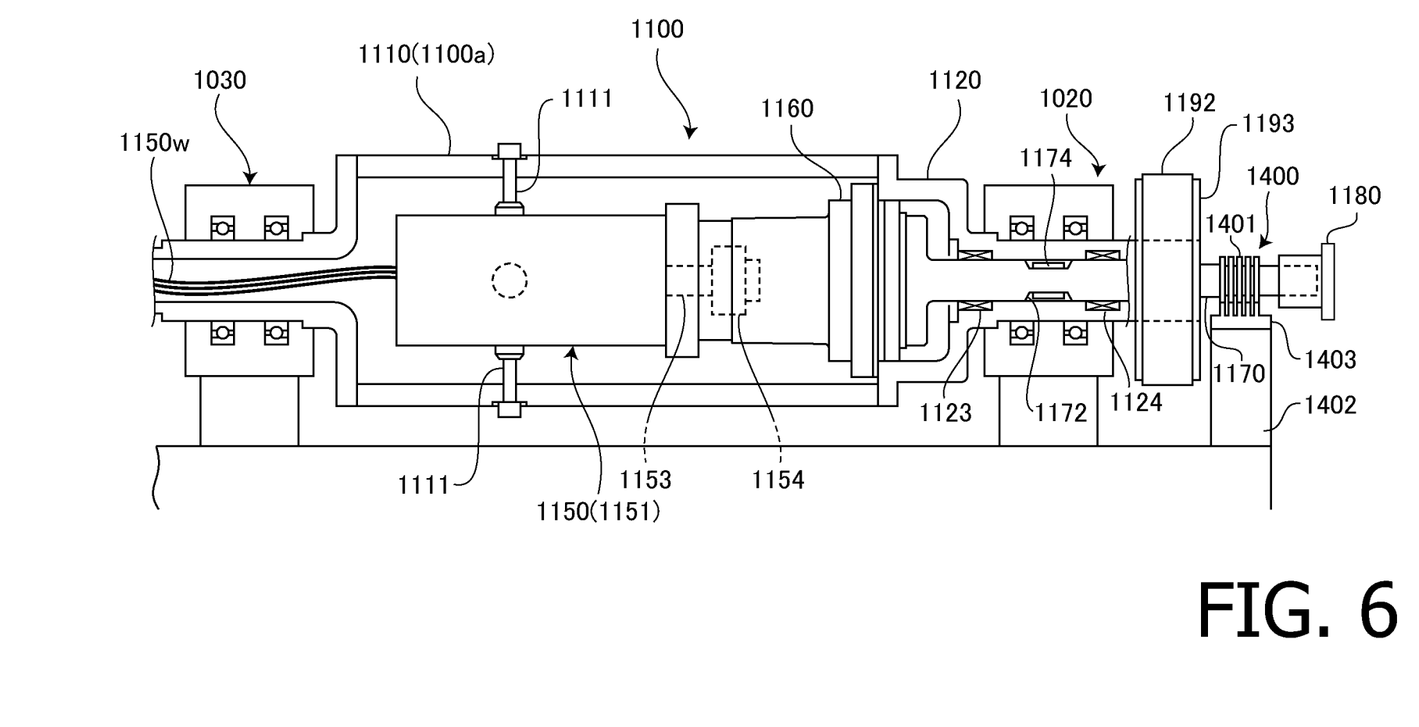
FIG. 6 is a vertical cross section of a load applying unit provided in the rotational torsion tester according to the second embodiment.

Hereafter, a rotational torsion tester 1000 according to a second embodiment of the invention is described. The rotational torsion tester 1000 is an apparatus for performing rotational torsion test for a propeller shaft for a vehicle being a test piece, and is able to apply set fixed or varying torque to a portion between an input shaft and an output shaft of the propeller shaft while rotating the propeller shaft. FIG. 4 is a plan view of the rotational torsion tester 1000, and FIG. 5 is a side view (a drawing viewed from the upper side in FIG. 4) of the rotational torsion tester 1000. FIG. 6 is a vertical cross section around a load applying unit 1100 described later. A control system of the rotational torsion tester 1000 has substantially the same configuration as that of the first embodiment shown in FIG. 3.

As shown in FIG. 4, the rotational torsion tester 1000 includes four bases 1011, 1012, 1013 and 1014 supporting each part of the rotational torsion tester 1000, the load applying unit 1100 which applies predetermined torque to a portion between both ends of the test piece T2 while rotating together with the test piece T2, bearing units 1020, 1030 and 1040 which rotatably supports the load applying unit 1100, slip ring parts 1050, 1060 and 1400 which electrically connects the inside and the outside wirings of the load applying unit 1100, a rotary encoder 1070 which detects the number of rotations of the load applying unit 1100, an inverter motor 1080 which drives and rotates an end of the load applying unit 1100 and the test piece T2 at a set rotation direction and the number of rotations, a drive force transmission unit 1190 (a drive pulley 1191, a drive belt (timing belt) 1192 and a driven pulley 1193) which transmits the driving force of the inverter motor 1080 to the load applying unit 1100, and a drive force transmission unit 1200 which transmits the driving force of the inverter motor 1080 to one end of the test piece T1. The drive force transmission unit 1200 includes a bearing unit 1210, a drive shaft 1212, a relay shaft 1220, a bearing unit 1230, a drive shaft 1232, a drive pulley 1234, a bearing unit 1240, a drive shaft 1242, a driven pulley 1244, a drive belt (timing belt) 1250 and a work attachment unit 1280.

The bearing units 1020, 1030 and 1040, the slip ring part 1050, the slip ring part 1060, the rotary encoder 1070, the inverter motor 1080 and the drive pulley 1091 provided in the rotational torsion tester 100 are the same as the bearing units 20, 30 and 40, the slip ring part 50, the slip ring part 60, the rotary encoder 70, the inverter motor 80 and the drive pulley 91 provided in the rotational torsion tester 1 according to the first embodiment. The load applying unit 1100 has the same configuration as that of the load applying unit 100 according to the first embodiment, excepting a shaft part 1120, a joint shaft 1170, a work attachment unit 1180 and a slip ring part 1400 which are described later. The drive belt 1192 is different from the drive belt 92 according to the first embodiment in that the drive belt 1192 is hooked to the driven pulley 1193 on the driven side, but the other structures of the drive belt 1192 are the same as those of the drive belt 92. In the following, to element which are the same as or similar to those of the first embodiment, the same or similar reference numbers are assigned and explanation thereof are omitted, and the explanation focuses on difference in the configuration from the first embodiment.

The four bases 1011, 1012, 1013 and 1015 are placed on a flat floor F, and are fixed with fixing bolts (not shown). On the base 1011, the inverter motor 1080 and the bearing unit 1210 are fixed. On the base 1012, the bearing units 1020, 1030 and 1040 which support the load applying unit 1100 and a support frame 1402 for the slip ring part 1400 are fixed. On the base 1013, the bearing unit 1230 is fixed. On the base 1014, the bearing unit 1240 is fixed. The bases 1013 and 1014 are movable in the axial directions of the bearing units 1230 and 1240, respectively, depending on the length of the test piece T1, by loosening the fixing bolts.

The joint shaft 1170 of the load applying unit 1100 projects outward from the tip (the right end in FIG. 6) of the shaft part 1120, and the work attachment unit (a flange joint) 1180 is fixed to the tip (the right end in FIG. 6) of the joint shaft 1170. To the projected part of the joint shaft 1170 from the shaft part 1120, the slip ring 1401 having a plurality of electrode rings is attached.

As shown in FIG. 6, at a part of the joint shaft 1170 included in the shaft part 1120, a ring-shaped narrowed part 1172 formed such that the outer diameter thereof is narrowed is formed, and a strain gauge 1174 is attached to a circumferential surface of the narrowed part 1172. The joint shaft 1170 is a cylindrical member having a hollow part (not shown) passing through the center axis thereof, and, in the narrowed part, an insertion hole (not shown) communicating with the hollow part is formed. A lead (not shown) of the strain gauge 1174 is inserted into the above described insertion hole and the hollow part formed in the joint shaft 1170, and is connected to each electrode ring of the slip ring 1401. It should be noted that, in place of the hollow part and the insertion hole, a wiring groove may be formed on the circumferential surface of the joint shaft 1170 to extend from the narrowed part 1172 to the slip ring 1401, and the lead of the stain gauge 11174 may be wired to the sip ring 1401 such that the lead passes through the wiring groove.

Under the slip ring 1401, a flange part 1403 fixed to the support frame 1402 is disposed. The flange part 1403 includes a plurality of flanges disposed to face and contact the respective electrode rings of the slip ring 1401. The terminal of each flange is connected to a torque measurement unit 1350 (which is described later) with a wire (not sown).

Hereafter, the drive force transmission unit 1200 (FIG. 4) is explained. The bearing units 1210, 1230 and 1240 rotatably support the drive shafts 1212, 1232 and 1242, respectively. One end (the left end in FIG. 4) of the drive shaft 1212 is coupled to the drive shaft of the inverter motor 1080 via the drive pulley 1191. One end (the left end in FIG. 4) of the drive shaft 1232 is coupled to the other end (the right end in FIG. 4) of the drive shaft 1212 via the relay shaft 1220. The drive pulley 1234 is attached to the other end (the right end in FIG. 4) of the drive shaft 1232, and the driven pulley 1244 is attached to one end (the right end in FIG. 4) of the drive shaft 1242. The drive belt 1250 is provided to extend between the drive pulley 1234 and the driven pulley 1244. The work attachment unit (flange joint) 1280 for fixing one end of the test piece T2 is attached to the other end (the left end in FIG. 4) of the drive shaft 1242.

The driving force of the inverter motor 1080 is transmitted to the work attachment unit 1280 via the above described drive force transmission unit 1200 (i.e., the drive shaft 1212, the relay shaft 1220, the drive shaft 1232, the drive pulley 1234, the drive belt 1250, the driven pulley 1244 and the drive shaft 1242), to rotate the work attachment unit 1280 at the set number of rotations and in the set rotational direction. At the same time, the driving force of the inverter motor 1080 is transmitted to the load applying unit 1100 via the drive force transmission unit 1190 (i.e., the drive pulley 1191, the drive belt 1192 and the driven pulley 1193), to rotate the load applying unit 1100 and the work attachment unit 1280 in a synchronized manner (i.e., constantly at the same speed and in the same phase).

Figure 7:
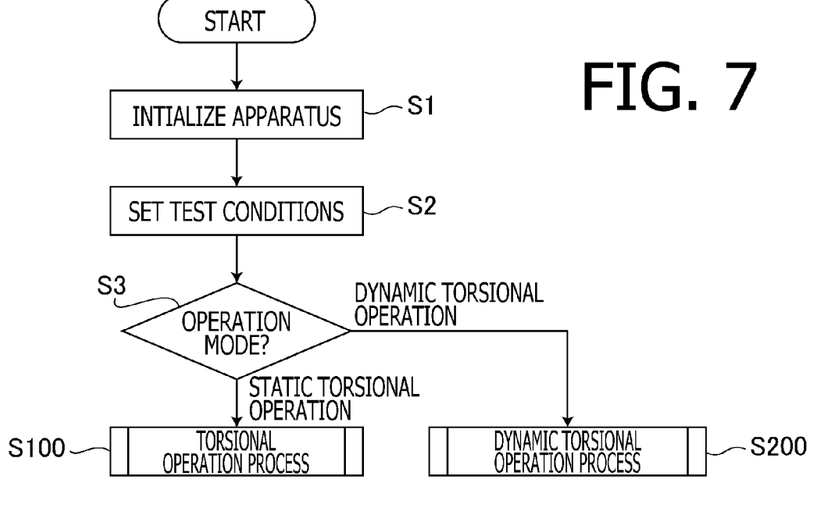
FIG. 7 is a flowchart illustrating a process executed by the rotational torsion tester according to the second embodiment.

Hereafter, function control of the rotational torsion tester 1000 according to the second embodiment is explained. The following is an example of the control of the function control of the rotation torsion tester 1000 according to the second embodiment, and it is also possible to apply the function control described below to the rotational torsion tester 1 according to the first embodiment. FIG. 7 is a flowchart of a process executed by the rotational torsion tester 1000. When the rotational torsion tester 100 is started, an initialization process S1 is executed for each component. Then, setting of the test condition is made by the setting unit 1370 (S2). Setting of the test condition is conducted by user input on an input screen (not shown). The test condition may be inputted by reading existing test condition data from a recording medium, such as a memory card, or from a server via a network. Alternatively, the test condition (e.g., a test waveform) may be inputted from an external device, such as a function generator.

Figure 8:
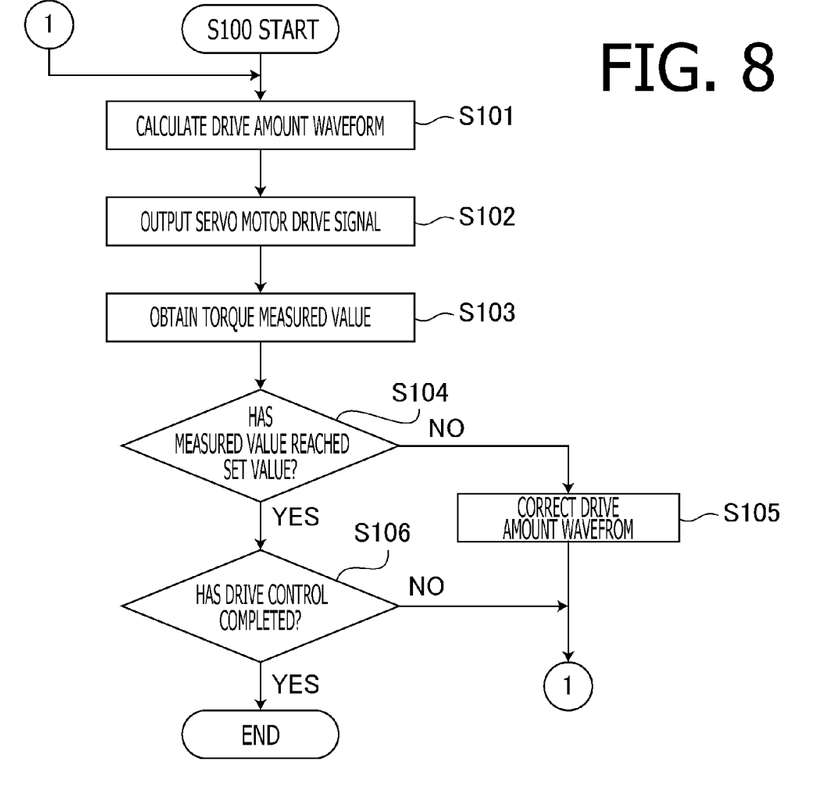
FIG. 8 is a flowchart illustrating a tortional operation process.
Figure 9:
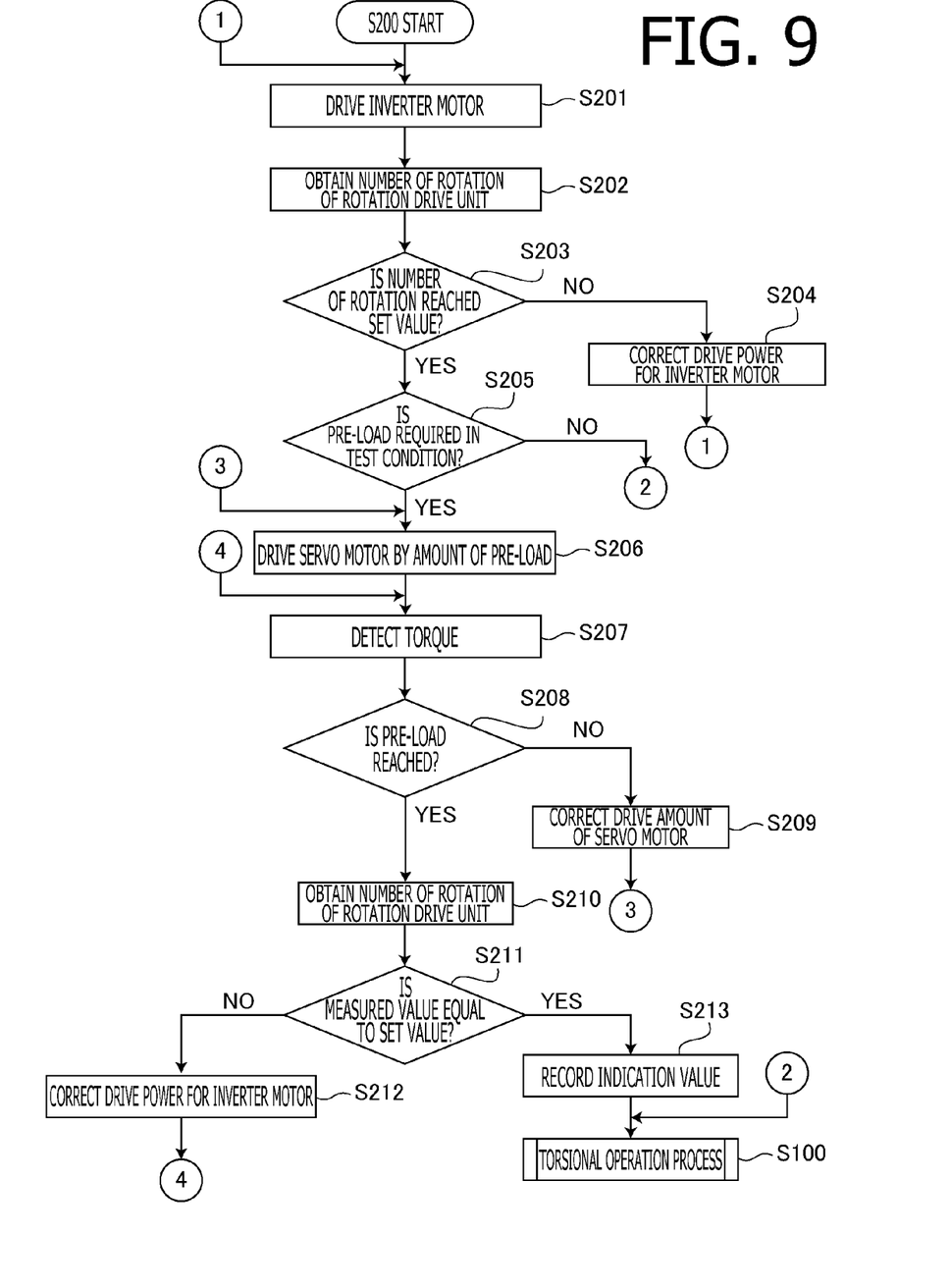
FIG. 9 is a flowchart illustrating a dynamic torsional operation process.

Next, the control unit 1310 judges whether an operation mode of the inputted test condition is "static torsional operation" or "dynamic torsional operation" (S3). The "static torsional operation" is an operation mode where torsion is given to the work in a state where the work is stationary without rotating, and is applied when a general torsion test is performed. The "dynamic torsional operation" is an operation mode where torsion is given to the work while the work is rotating, and is applied to the rotational torsion test. When the operation mode of the set test condition is the static torsional operation, a "torsional operation process" (S100) shown in FIG. 8 is executed. When the operation mode of the set test condition is the dynamic torsional operation, a "dynamic torsional operation process" (S200) shown in FIG. 9 is executed.

In the torsional operation process S100 (FIG. 8), first a drive amount waveform calculation process S101 in which a waveform of the inputted test torque is converted into a waveform of the drive amount of the servo motor 1150 is executed. The drive amount waveform calculation process S101 is executed by a waveform generation unit 1320 which is able to execute a calculation process at a high speed. Next, the control unit 1310 outputs a drive signal representing an indication value of the drive amount corresponding to each time based on the drive amount waveform calculated in the process S101, to the servo motor drive unit 1330, to drive the servo motor 1150 (S102). Ten, the control unit 1310 obtains the measured value of the torque given to the test piece T2 from the torque measurement unit 1350 (S103). Next, the waveform generation unit 1320 judges whether the measured value of the torque obtained in the process S103 has reached a set value (S104). When the measured value of the torque has not reached the set value (S104: NO), the waveform generation unit 1320 corrects the drive amount waveform in a feedback manner (S105), and the control unit 1310 outputs the drive signal again based on the new drive amount waveform to drive the servo motor 1150 (S102). When the measured value of the torque has reached the set value (S104: YES), the control unit 1310 judges whether the drive control has completed to the end of the drive waveform (S106). When the drive control has not completed to the end of the drive waveform, the process returns to S102 to continue the drive control. When the drive control has completed, the process S100 terminates.

The above described torque control is an example where the torque given to the test piece T1 is controlled; however, the rotational torsion tester 1000 may execute displacement control where the torsion angle (displacement) given to the test piece T1 is controlled. When the displacement control is executed, the waveform of the test displacement (torsion angle) is converted into the waveform of the drive amount of the servo motor 1150 in the drive amount waveform calculation process S101. Furthermore, the waveform generation unit 1320 calculates the measured value of the torsion angle given to the test piece T1 from the signal of the built-in rotary encoder provided in the servo motor 150 in S103, and judges whether the measured value of the torsion angle reaches the set value in S104.

Figure 10:
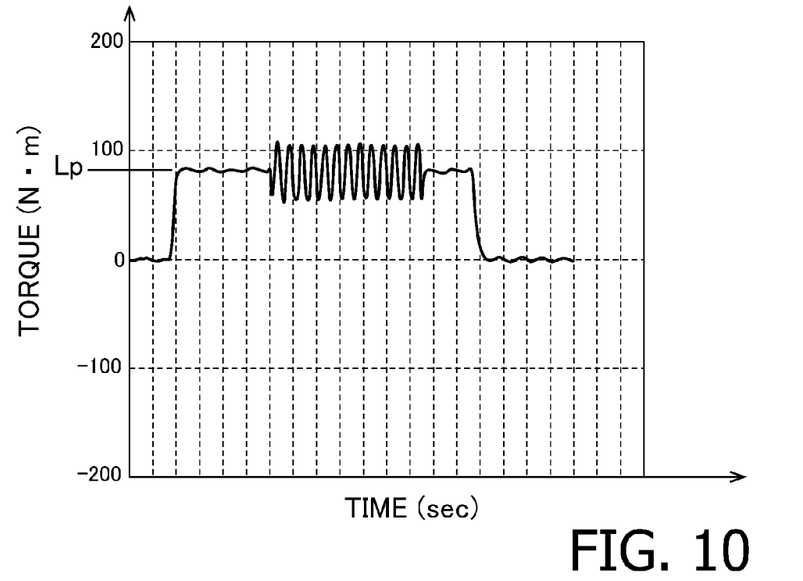
FIG. 10 is a graph illustrating torque applied to a test piece in the torsional operation process.
Figure 11:
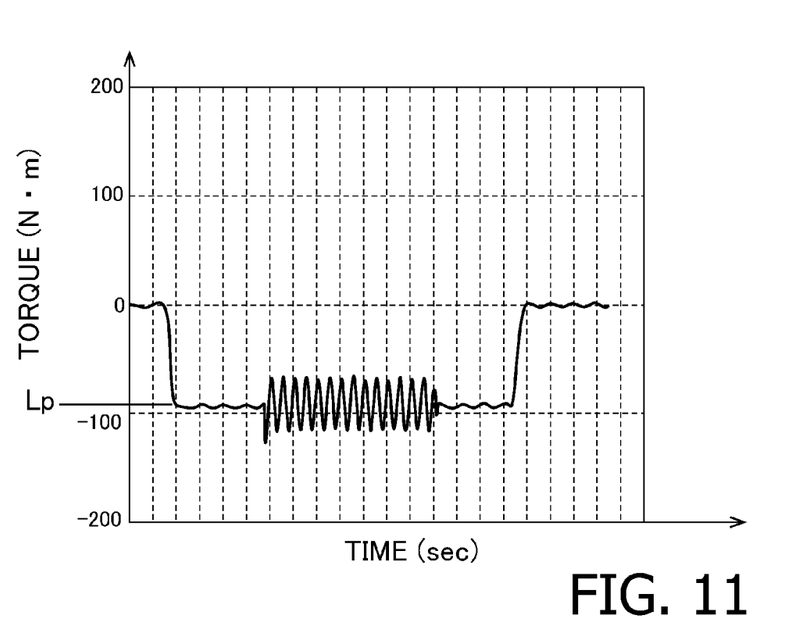
FIG. 11 is a graph illustrating torque applied to the test piece in the dynamic torsional operation process.

In the dynamic torsional operation process S200 (FIG. 9), first the inverter motor 1080 is driven so that the test piece T2 rotates at the set number of rotations (S201). Then, the measured value of the number of rotations of the load applying unit 1100 rotated by the inverter motor 1080 together with the test piece T2 is obtained from the rotation number calculation unit 360 (S202). Then, the control unit 1310 judges whether the obtained measured value of the number of rotations of the load applying unit 1100 has reached the set value (S203). When the measured value has not reached the set value (S203: NO), the drive power (frequency) of the inverter motor 1080 is corrected (S204). When the measured value of the number of rotations of the load applying unit 1100 has reached the set value (S203: YES), the process proceeds to S205. In S205, the control unit 1310 judges whether the test condition requires applying of a pre-load (torque) Lp to the test pieces T2. The pre-load Lp means a DC component (static load) of the torque applied to the test piece T2. For example, for rotational torsion test for simulating a braking operation, the pre-load Lp in the reverse direction (minus) of the rotation direction by the inverter motor 1080 is applied (FIG. 10). For rotational torsion test simulating a traveling test at a constant acceleration, the pre-load Lp in the same direction (plus) as the rotation direction by the inverter motor 1080 is applied (FIG. 11).

When the pre-load Lp is applied (S205: YES), the drive amount corresponding to the pre-load Lp is assigned to the indication value, and the servo motor 1150 is driven so that only the pre-load Lp is applied to the test piece T2 (S206). Then, the measured value of the torque given to the test piece T2 is obtained from the torque measurement unit 1350 (S207), and the control unit 1310 judges whether the measured value reaches the set value of the pre-load (S208). When the measured value of the torque has not reached the set value of the pre-load Lp (S208: NO), the control unit 1310 corrects the indication value of the drive amount of the servo motor 1150 (S209), and drives the servo motor 1150 again based on the corrected indication value (S206).

The pre-load Lp changes the number of rotations of the inverter motor 1080 because the pre-load Lp also places a load on the inverter motor 1080. For this reason, the control unit 1310 obtains again the measured value of the number of rotations of the load applying unit 1100 (S219), and judges whether the measured value is equal to the set number of rotations (S211). When the measured value of the number of rotations is not equal to the set value (S211: NO), the control unit 1310 corrects the frequency of the drive power of the inverter motor 1080 so that the difference with respect to the set value is cancelled (S212). When the frequency of the drive current of the inverter motor 1080 is corrected and the number of rotations of the load applying unit 1100 changes, the torque given to the test piece T2 also changes. Therefore, by detecting the torque again (S207), the control unit 1301 judges whether the pre-load equal to the set value is properly applied (S208).

When it is judged that the measured value of the number of rotations of the load applying unit 1100 obtained in S211 is equal to the set value (S211: YES), the control unit 1310 stores the indication value being used for the drive instruction for the inverter motor 1080 and the servo motor 1150 in a memory (S213). Then, the process proceeds to the torsional operation process S100 in the state where the preload Lp is being applied.

For the test condition where the pre-load Lp is not applied (S205: NO), the process directly proceeds to the torsional operation process S100.

Furthermore, for the test condition where the pre-load Lp is applied, the test torque is divided into a DC component (static load) and an AC component (dynamic load), and the calculation for the drive amount waveform is executed only for the AC component. Then, a value defined by adding the drive amount which gives the AC component calculated in S101 to the drive amount necessary for applying the pre-load stored in S212 is set as the indication value for the servo motor 1150. For the drive control of the inverter motor 1080, the indication value stored in S212 is used.

The foregoing is the explanations about the exemplary embodiments of the invention. It should be noted that the present invention is not limited to the above described embodiments, and may be varied within the scope of the invention expressed in the claims.

In the above described embodiment, the driving force of the servo motor is amplified by the reduction gear; however, the reduction gear may be omitted as long as a servo motor capable of outputting an adequately large degree of torque is used. By thus omitting the reduction gear, a frictional loss can be reduced, and the moment of inertia of the driving part of the rotational torsion tester can be reduced. As a result, the reversed driving at a higher frequency can be realized.

In the above described embodiment, the timing belt is used to transmit the driving force between the rotation shafts arranged in parallel with each other; however, an endless belt of another type (e.g., a flat bet or a V belt) may be used. A driving force transmission mechanism (e.g., a chain mechanism or a gear mechanism) other than the endless belt may be used.

In the above described second embodiment, the driven pulley 1193 is disposed on the work attachment part 1180 side with respect to the bearing unit 1020. With this configuration, the interval between the driven pulleys 1193 and the 1244 can be shortened, and the drive transmission part can be realized in a compact size. In the second embodiment, the driven pulley 1244 is disposed on the opposite side of the work attachment unit 1280 with respect to the bearing unit 1240; however, the driven pulley 1244 may be disposed on the work attachment unit 1280 side with respect to the bearing unit 1240. Such a configuration also makes it possible to realize the compact driving force transmission unit. The driven pulley 1193 may be disposed on the opposite side of the work attachment unit 1180 with respect to the bearing unit 1020. By disposing the bearing unit 1020 between the driven pulley 1193 and the work attachment unit 1180, the vibration noise in directions other than the rotational direction from the drive force transmission unit 1190 to the test piece T2 can be prevented, and therefore a more precise testing can be achieved.

In the above described embodiment, the control unit provides a command signal in a form of a digital code with the servo motor drive unit and the inverter motor drive unit; however, a command signal (e.g., an analog current signal, an analog voltage signal or a pulse signal) in another form may be given to each drive unit.

In the above described embodiment, driving of the servo motor is controlled by controlling the rotation angle (displacement) of the drive shaft of the servo motor or the torque given to the test piece; however, embodiments of the invention are not limited to such a configuration, and control in which another type of parameter (e.g., a rotation speed of the servo motor or the torsional speed of the test piece) is used as a target value is also included in the scope of the invention.

In the above described first embodiment, the torque sensor 172 is disposed on the outside of the bearing unit 20; however, as in the case of the second embodiment, a ring-shaped narrowed part formed to have a thin outer diameter may be provided at a part of the joint shaft 170 accommodated in the bearing unit 20, and a strain gauge may be adhered to the narrowed part so that a torque sensor is disposed in the bearing unit 20.

What is claimed is:

1. A rotational torsion tester, comprising:
a first drive shaft that rotates about a predetermined rotation axis, an end of a workpiece being attached to the first drive shaft;
a second drive shaft that rotates about the predetermined rotation axis, the other end of the workpiece being attached to the second drive shaft;
a load applying unit that applies a torsional load to the workpiece by driving and rotating the first drive shaft;
at least one bearing unit including a first bearing unit that supports the load applying unit to be rotatable about the predetermined rotation axis;
a rotation drive unit having a first electric motor that drives the second drive shaft and the load applying unit to rotate in phase; and
a torque sensor that detects the torsional load,
wherein:
by causing the rotation drive unit to rotate the workpiece via the first drive shaft and the second drive shaft and by causing the load applying unit to give a phase difference to rotations of the first drive shaft and the second drive shaft, a load is applied to the workpiece;
the load applying unit comprises: a second electric motor that drives the first drive shaft; and a frame having a cylindrical shaft part into which the first drive shaft is inserted;
the frame is supported by the first bearing unit at the shaft part and the frame supports the first drive shaft;
the torque sensor is attached to a part at which the first drive shaft is inserted into the shaft part, and detects the torsional load at the part;
the shaft part includes a pair of first bearings which are disposed to be away from each other in an axial direction and rotatably support the first drive shaft;
the torque sensor is disposed between the pair of first bearings;
a narrowed part formed to have a decreased diameter is formed at the part at which the first drive shaft is situated in the shaft part; and
the torque sensor includes a strain gauge adhered to the narrowed part to detect the torsional load.

2. The rotational torsion tester according to claim 1, wherein:
the first bearing unit comprises a pair of second bearings which are disposed to be away from each other in the axial direction and rotatably support the shaft part; and
the torque sensor is disposed between the part of second bearings.

3. The rotational torsion tester according to claim 1, wherein the load applying unit comprises a drive amount detection unit configured to detect a drive amount of the second electric motor.

4. The rotational torsion tester according to claim 3, further comprising:
a drive power supply unit that is disposed outside the load applying unit and is configured to supply driving power to the second electric motor;
a drive power transmission line configured to transmit the driving power from the drive power supply unit to the second electric motor;
a torque signal processing unit that is disposed outside the load applying unit and is configured to process a torque signal outputted by the torque sensor; and
a torque signal transmission line configured to transmit the torque signal from the torque sensor to the torque signal processing unit,
wherein the drive power transmission line comprises:
an outer drive power transmission line disposed outside the load applying unit;
an internal drive power transmission line that is disposed in an inside of the load applying unit and is configured to rotate together with the load applying unit; and
a first slip ring part that connects the outer drive power transmission line with the internal drive power transmission line,
wherein the torque signal transmission line comprises:
an outer torque signal transmission line disposed outside the load applying unit;
an internal torque signal transmission line that is disposed in an inside of the load applying unit and is configured to rotate together with the load applying unit; and
a second slip ring part that connects the outer torque signal transmission line with the internal torque signal transmission line, and
wherein the second slip ring part is disposed to be away from the first slip ring part.

5. The rotational torsion tester according to claim 4, wherein the at least one bearing unit is disposed between the first slip ring part and the second slip ring part.

6. The rotational torsion tester according to claim 4, wherein:
the shaft part has a groove extending in the axial direction from the narrowed part; and
the internal torque signal transmission line is formed to pass through the groove from the narrowed part, and is connected to a ring-shaped electrode of the second slip ring part.

7. The rotational torsion tester according to claim 6, further comprising a drive amount signal transmission line configured to transmit a signal outputted by the drive amount detection unit to the drive power supply unit,
wherein the drive amount signal transmission line comprises:
an outer drive amount signal transmission line disposed outside the load applying unit;
an internal drive amount signal transmission line that is wired in an inside of the load applying unit and is configured to rotate together with the load applying unit; and
a third slip ring part that is disposed to be away from the first slip ring part and is configured to connect the outer drive amount signal transmission line with the internal drive amount signal transmission line.

8. The rotational torsion tester according to claim 4, further comprising a rotation number detection unit configured to detect a number of rotations of the load applying unit,
wherein the at least one bearing unit is disposed between the rotation number detection unit and the first slip ring part.

9. The rotational torsion tester according to claim 1,
wherein the rotation drive unit comprises a drive force transmission unit configured to transmit a driving force of the first electric motor to the load applying unit and the second drive shaft,
wherein the drive force transmission unit comprises:
a first drive force transmission unit configured to transmit the driving force of the first electric motor to the second drive shaft; and
a second drive force transmission unit configured to transmit the driving force of the first electric motor to the load applying unit.

10. The rotational torsion tester according to claim 9,
wherein each of the first drive force transmission unit and the second drive force transmission unit comprises at least one of an endless belt mechanism, a chain mechanism and a gear mechanism.

11. The rotational torsion tester according to claim 10,
wherein each of the first drive force transmission unit and the second drive force transmission unit comprises the endless belt mechanism,
wherein the first drive force transmission unit comprises:
a third drive shaft that is disposed to be parallel with the predetermined rotation axis and is configured to be driven by the first electric motor;
a first drive pulley fixed to be coaxial with the third drive shaft;
a first driven pulley fixed to be coaxial with the load applying unit; and
a first endless belt provided to extend between the first drive pulley and the first driven pulley, and
wherein the second drive force transmission unit comprises:
a fourth drive shaft that is coaxially coupled to the third drive shaft;
a second drive pulley fixed to the fourth drive shaft;
a second driven pulley fixed to the first drive shaft; and
a second endless belt provided to extend between the second drive pulley and the second driven pulley.

12. The rotational torsion tester according to claim 11,
wherein the first driven pulley is formed on an outer circumferential surface of the frame of the load applying unit.

13. The rotational torsion tester according to claim 11, further comprising a reduction gear disposed in the load applying unit,
wherein the first driven pulley is fixed to a reduction gear fixing plate to which the reduction gear is attached.

14. The rotational torsion tester according to claim 1,
wherein the first drive shaft and the frame of the load applying unit are connected to each other coaxially and integrally.

15. The rotational torsion tester according to claim 14,
wherein the frame of the load applying unit has a cylindrical part whose outer circumferential surface is formed in a cylindrical shape to be coaxially with the predetermined rotation axis,
wherein the rotational torsion tester further comprises:
a third drive shaft that is disposed to be parallel with the predetermined rotation axis and is configured to be driven by the first electric motor;
a first drive pulley fixed to the third drive shaft; and
a timing belt wound around the first drive pulley and the cylindrical part of the frame.

* * * * *